(12) United States Patent
Musco et al.

(10) Patent No.: US 9,724,376 B2
(45) Date of Patent: Aug. 8, 2017

(54) OLIVE LEAF POWDER

(71) Applicants: Freedame LLC, Livermore, CA (US);
The United States of America as Represented by the Secretary of the Department of Agriculture, Washington, DC (US)

(72) Inventors: Josephine Musco, Livermore, CA (US); Tara H. McHugh, Albany, CA (US); Zhongli Pan, Davis, CA (US); Roberto Avena-Bustillos, Davis, CA (US)

(73) Assignees: Josephine Musco, Livermore, CA (US); The United States of America as Represented by the Secretary of the Department of Agriculture, Washington, DC (US)

( * ) Notice: Subject to any disclaimer, the term of this patent is extended or adjusted under 35 U.S.C. 154(b) by 0 days.

(21) Appl. No.: 14/687,329

(22) Filed: Apr. 15, 2015

(65) Prior Publication Data

US 2016/0106128 A1 Apr. 21, 2016

Related U.S. Application Data

(60) Provisional application No. 62/064,836, filed on Oct. 16, 2014.

(51) Int. Cl.
| | | |
|---|---|---|
| *A61K 36/63* | (2006.01) | |
| *A61K 8/97* | (2017.01) | |
| *A01N 65/08* | (2009.01) | |
| *A61K 8/02* | (2006.01) | |
| *A01N 25/12* | (2006.01) | |
| *A61K 9/14* | (2006.01) | |
| *A01N 65/00* | (2009.01) | |
| *A23L 3/3472* | (2006.01) | |
| *A23L 5/10* | (2016.01) | |
| *A23L 19/00* | (2016.01) | |
| *A23L 33/105* | (2016.01) | |
| *A61Q 17/00* | (2006.01) | |
| *A61Q 17/04* | (2006.01) | |

(52) U.S. Cl.
CPC .............. *A61K 36/63* (2013.01); *A01N 25/12* (2013.01); *A01N 65/00* (2013.01); *A01N 65/08* (2013.01); *A23L 3/3472* (2013.01); *A23L 5/15* (2016.08); *A23L 19/01* (2016.08); *A23L 33/105* (2016.08); *A61K 8/022* (2013.01); *A61K 8/97* (2013.01); *A61K 9/14* (2013.01); *A61Q 17/005* (2013.01); *A61Q 17/04* (2013.01)

(58) Field of Classification Search
None
See application file for complete search history.

(56) References Cited

U.S. PATENT DOCUMENTS

2006/0034981 A1    2/2006  Pan et al.

OTHER PUBLICATIONS

Boudhrioua (Industrial Crops and Products (2009), vol. 29, pp. 412-419).*
Vishwanathan (Food and Bioproducts Processing (2013), vol. 91, pp. 89-94).*

* cited by examiner

*Primary Examiner* — Susan Hoffman
(74) *Attorney, Agent, or Firm* — Kilpatrick Townsend & Stockton LLP

(57) ABSTRACT

The present invention provides methods of producing high quality olive leaf powders using infrared dry blanching, drying, and milling. Also provided are powders prepared by the methods of the invention. The powders can be included in various food, pharmaceutical, cosmetic, and antimicrobial compositions.

20 Claims, No Drawings

OLIVE LEAF POWDER

CROSS-REFERENCE TO RELATED APPLICATIONS

The present application claims priority under 35 U.S.C.§119(e) to U.S. Application No. 62/064,836, filed Oct. 16, 2014.

FIELD OF THE INVENTION

The present invention relates to methods of producing high quality olive leaf powders. The components of olive leaves (*Olea europaea*) are known to provide a range of health benefits. The powders of the invention are useful in any context in which the benefits of olive leaves are desired.

BACKGROUND OF THE INVENTION

Olive leaves are a source of a number of beneficial compounds. For example, they are known to comprise oleuropein, which is potent antioxidant and has been shown to have antibacterial, antiviral and antifungal activity. Oleuropein has also been shown to lower blood pressure and inhibit the oxidation of lipids in the blood, thereby lowering the risk of cardiovascular disease. Additional health promoting compounds found in olive leaves include luteolin-7-glucoside, verbascoside, and apigenin-7-glucoside. Olive leaves also contain anti-cancer compounds, such as apigenin and luteolin, as well as the anti-malarial agent cinchonine.

Olive leaf extract also has anti-inflammatory, as well as antiseptic properties. Evidence suggests that olive leaf extract may protect against nerve damage, and may be of value in cases of stroke. Both the leaves and the bark can be used to treat fever.

Olive leaf extracts are useful for the treatment of some skin conditions. Olive leaf extracts have been shown to promote wound healing, prevent the growth of skin cancer cells, and protect against sun damage.

In view of the many health benefits provided by olive leaves, there is a recognized need for preparing olive leaf products for use in food, pharmaceutical, cosmetic, and antimicrobial products. The present invention addresses these and other needs.

BRIEF SUMMARY OF THE INVENTION

The present invention provides methods of producing high quality olive leaf powders. The methods comprise blanching fresh olive leaves using infrared radiation, drying the blanched olive leaves, and milling the dried olive leaves to produce the flavorful, colorful and nutritious olive leaf powder.

The infrared blanching typically uses radiation having a wavelength between 3 and 8 microns, usually about 4.5 microns. It is carried out for 30 seconds to 5 minutes, usually for about 1.5 minutes. In the typical embodiment, the infrared blanching results in a surface temperature on the olive leaves of between 200° F. and 300° F., usually about 260° F.

The drying step is usually carried out using hot air drying at a temperature between 70° C. and 95° C., more often about 80° C. The drying can be carried out for between about 15 and about 40 minutes, usually about 30 minutes.

The milling step may be preceded by separating the leaf blades from the leaf midrib and petioles and/or grinding the olive leaves. The milling usually results in a powder with a particle size less than about 500 microns, often less than about 200 microns.

The invention also provides leaf powder produced by the method of the invention, as well as food, pharmaceutical, cosmetic and antimicrobial products comprising the powder.

DETAILED DESCRIPTION OF THE INVENTION

The present invention provides a novel process to produce high quality olive leaf powders. By combining infrared blanching and drying (e.g., hot-air drying), a high quality olive leave powder is produced. The properties of this powder are superior to those of powders produced by conventional methods such as freeze drying and hot air drying, a process that was previously thought to produce the highest quality food products. Surprisingly, by combining infrared blanching and hot air drying, olive leaf powders with improved bright green color, flavor, aroma and solubility are produced. The powders of the invention also exhibit increases in total soluble phenolics and antioxidant capacity.

Dehydrated olive leafs are being commercially produced, but commercial products have low product quality. Infrared dry blanching can be achieved under controlled conditions in thin layers of moist olive leaves by exposing leaves for short periods of time to regulated continuous or intermittent infrared heating. Infrared dry blanching process also reduces moisture content of leaves resulting in reduced drying time. Hot air drying results in consistently higher soluble phenolics and antioxidant capacity and reduced bitterness compared with freeze-drying.

Dried whole olive leaves can be mechanically brokendown and their fractions separated by density differences or vibrating tilted platforms into two main components, petioles (and midribs) and blades. Comparing leaf blade (without petioles and midribs) olive tea against tea made with whole leaves indicated that the former has a less bitter flavor, more distinct aroma, a greener color and significantly higher antioxidant capacity.

Reducing the particle size of the powders using standard milling equipment, such as rotary impeller cyclone mills with 500 micron to 250 micron screens by multiple passes, helps to increase solubility and homogeneity as well as improve the color of solutions, without reducing antioxidant capacity of the olive leaf powders.

Packaging of olive leaf powders of the invention in low oxygen permeability packaging films with a nitrogen headspace reduces browning and oxidation during distribution and storage, preserving high antioxidant values until time of consumption.

This novel technology achieves similar antioxidant capacity with improved solubility and suspension compared to high quality commercial green tea powders and superior quality compared with commercial olive leaf teas, powders, extracts, and supplements currently on the market. This combined technology will allow the use of a plentiful supply of a high antioxidant value crop by-product from olive trees.

The powders of the invention can be used as a basis to manufacture a variety of different food products including but not limited to teas, supplements, nutritional bars and drinks, baby food ingredients, elixirs, pastes, coatings, as well as pharmaceuticals, cosmetics, pesticides, or any olive leaf product in which enhanced antioxidant and antimicrobial properties are desired.

A. Infrared Blanching

Blanching is a procedure used to inactivate enzymes responsible for quality deterioration of various food products, such as fruits and vegetables. This inactivation is normally achieved by exposing fruits and vegetables to an elevated temperature (e.g., 70 to 100° C.). Besides inactivating enzymes, blanching also reduces microbial contamination, stabilizes color, and facilitates further processing and handling.

The methods of the present invention rely on infrared dry blanching. Methods for infrared dry blanching of food products are described in US2006/0034981, which is incorporated herein by reference. Infrared blanching is an improvement over steam, water and/or microwave blanching methods, which can cause undesirable changes in food products.

Infrared dry blanching technology works by using infrared radiation energy to heat-up food products, achieving blanching and dehydration in a single step Infrared dry blanching can be combined with heated air or vacuum to accelerate the drying process.

Means for generating infrared radiation of the desired wavelength are well known to those of skill in the art. For example, a Catalytic flameless gas-fired (CFG) infrared emitter from Catalytic Infrared Drying Technologies LLC (Independent, KS) can be used. One of skill will recognize that a number of parameters can be varied to achieve the desired degree of blanching. Depending on specific wavelength range, infrared energy generally is divided into the following categories: near infrared (0.8-2 µm), medium infrared (2-4 µm) and far infrared (4-100 µm). In the methods of the invention, the infrared radiation typically has a wavelength between 3 and 8 microns, usually about 4.5 microns. The blanching can be carried out from about 30 seconds to about 5 minutes. In a typical embodiment, from about 30 seconds to about 2 minutes, usually from about 1 minute to about 2 minutes. In general, a surface temperature on the olive leaves of between 200° F. and 350° F. is achieved, typically from about 250° F. to about 300° F., usually about 260° F.

B. Drying

After the olive leaves are blanched the leaves can be dried using any method known to those in the art. Such methods include, for example, hot air drying, dehydration with air flow, foodbed drying, sun drying, vacuum drying, microwave drying and freeze drying. A preferred method of drying is hot air drying. The hot air drying can be carried out at a temperature between 70° C. and 95° C., usually about 80° C. Drying time can be between about 15 and about 40 minutes, usually between about 25 and 35minutes. Final moisture content should be less than about 5%, usually less than about 3%.

C. Milling

After the material is dried, it is milled to produce a powder using standard milling equipment well known to those of skill in the art (e.g., rotary impeller cyclone mills). The resulting powder can be classified to the desired particle size using known sieving techniques. For example, a particle size distribution in a range of less than about 100 microns to less than 500 microns can achieved using standard sieving techniques. In the typical embodiment, the particles are less than about 250 microns, usually less than about 200 microns.

In some embodiments, the dried leaves are pre-ground prior to the milling step, to make the milling more efficient. In addition, the midribs and petioles can be separated from the leaf blades to improve the quality of the final product.

D. Preparation of Food Products and Pharmaceutical Compositions

The present invention also provides food products containing the olive leaf powders to the invention. Such food products include, for example, various general food products, teas, supplements, nutritional bars and drinks, baby food ingredients, elixirs, pastes, coatings, and the like.

The food product of the invention may contain additional components well known to those in the art. The additional components may include, for example, synthetic and natural flavoring agents and natural carbohydrates (e.g., glucose, fructose, sucrose and the like). The food products may also comprise various nutrients, vitamins, minerals (electrolytes), colorants stabilizers, alcohols, carbonating agents used in carbonated drinks, and the like.

The powders of the invention can be added to foods or beverages for the purpose of obtaining a desired health effect. In a typical embodiment, the food product or beverage may comprise from about 0.1% to about 100% by weight based on the total weight of the food.

E. Preparation of Pharmaceutical Compositions

The pharmaceutical compositions containing the olive leaf powder of the invention can be formulated into oral formulations such as powders, granules, tablets, capsules, suspensions, emulsions, and syrups, according to conventional methods.

Examples of solid preparations for oral administration include tablets, pills, powders, granules, capsules and the like. Solid preparations are prepared using at least one excipient, for example, starch, calcium carbonate, sucrose or lactose, gelatin and the like. Examples of liquid preparations for oral administration include suspensions, liquids for internal use, emulsions, syrups and the like. Liquid preparations may include various excipients, for example, wetting agents, sweeteners, fragrances, preservatives and the like, in addition to water.

The powders of the invention can be included in pharmaceutical compositions for the purpose of obtaining a desired health effect. In a typical embodiment, the composition may comprise from about 0.1% to about 100% by weight based on the total weight of the food.

F. Preparation of Cosmetic Compositions

The powders of the invention can also be used to prepare cosmetic compositions for topical use. Preparation of cosmetic compositions is well known to those of skill in the art. Such compositions may comprise, for example, at least one humectant (e.g., polyhydric alcohols such as glycerine, propylene glycol, dipropylene glycol, and the like), and at least one thickener (e.g., fatty acids, fatty alcohols, carboxy methyl cellulose, xanthan gum, guar gum and the like). Other components may include botanical extracts, fragrance, sunscreens, vitamins (e.g., vitamin E), and the like.

The powders of the invention can be added to cosmetic composition for the purpose of obtaining a desired health effect. In a typical embodiment, the composition may comprise from about 0.1% to about 100%, usually by weight based on the total weight of the composition.

G. Preparation of Antimicrobial Compositions

The powders of the invention can also be used to prepare antimicrobial compositions for control of various microorganisms, such as bacteria and fungi. The antimicrobial compositions are suitable for inhibiting the growth of microorganisms in various products and compositions that normally support the growth of microorganisms. The olive leaf powder can be admixed with various compositions such as cosmetics and food products or applied to the surface of the food or other product to prolong the storage and shelf life.

The antimicrobial compositions can also be applied to the surface of an object to inhibit contamination.

The antimicrobial compositions of the invention typically comprise a suitable carrier or vehicle. The carrier is typically a liquid, solid, gel or paste. Examples of suitable carriers for the antimicrobial agent include water glycerol, ethanol, mineral oil and the like. The composition can also contain suitable humectants such as sorbitols and polyethylene glycols depending on the intended use. The composition can also be in the form of a topical liquid, lotion, cream or gel for applying topically to the skin of a patent in need of treatment with the antimicrobial agent. The antimicrobial composition may also contain binders or thickening agents such as silica precipitates, carboxymethylcellulose, carboxyvinyl polymers, xanthan gum and carrageenan gum. Suitable surfactants include sodium lauryl sulfate and dodecylbenzene sulfonate. Flavorants, fragrances and anti-caking agents, as known in the art, can also be included.

The powders of the invention can be added to antimicrobial composition for the controlling growth of microorganisms. In a typical embodiment, the composition may comprise from about 0.1% to about 100%, by weight based on the total weight of the composition.

EXAMPLE

IR Dry-Blanching

IR blanching when done without overlapping olive leaves and without water drops on their surface achieved very fast enzymatic inactivation resulting in higher total soluble phenolics and antioxidant capacity as well as higher health promoting flavonoids and phenylethanoids compared with steam blanched and un-blanched olive leaf powders. Steam blanching for 10 minutes condensed 1.4 mL of steam/g of olive leaves blanched. IR blanching can be done with less energy requirements and without the need of steam or water, allowing water and energy savings during the blanching and drying processes.

| Process | Infrared Blanching |
|---|---|
| Lead Time | 1:15 minutes IR heating on trays (2806 cm$^2$) with 0.392 kg/m$^2$ load density in manual IR system (3.3 kg leaves/h) and 0.216 kg/m$^2$ in IR mobile unit (36 kg/h in a heating section of 90 × 60"). |
| Labor | Half hour needed to blanch 20 kg of olive leaves with one person if using and automatic feeding into the IR mobile unit. |
| Machinery | IR mobile unit. |
| Conditions | 1.5 inch water column gas pressure, 100% propane flow (3.37 kg/h for 161,804 BTU/h). Mean and standard deviation of surface temperatures of IR emitters, Teflon belt and olive leaves are 693.4 ± 101.5, 484.5 ± 52.3, and 257.9 ± 13.8° F., respectively. Residence time of leaves inside the IR heating zone at 4.5 μm IR wavelength is 1 minute and 10 seconds at 42 Hz belt frequency for the IR mobile unit. |
| Limitations | Uniform blanching achieved when leaves overlapping and excess surface water is reduced. |

Hot Air Drying

Four trays of the cabinet dryer hold 880-900 g of blanched olive leaves. Drying was done in 35 minutes at 80° C. Assuming 10 minutes for loading and unloading trays, in an 8 h shift it is possible to do 10 drying batches. Using one drying cabinet in the Pilot Plant we can process 7 kg of fresh leaves/day (approximately 10 kg/day of olive branches considering leaves separation, sorting and waste)

| Process | Hot-air Drying |
|---|---|
| Lead Time | 35-40 minutes in cross-flow hot air at 80° C. in perforated trays |
| Labor | One person to load and unload drying trays |
| Machinery | Proctor & Schwartz Mod. 062 food cabinet dryer heated with steam. The dryer set for 80° C. (176° F.). These cabinet driers are also available to use natural gas for heating the air instead of steam that requires an additional boiler for steam production. |
| Conditions | Four trays (75.5 × 50 cm = 3775 cm$^2$) with 0.0588 g/cm$^2$ load density. 0.456 Kg of dried olive leaves/Kg of fresh olive leaves. Final moisture: 2.9%. Ratio Fresh:Dry = 1.8; Ratio Dry:Fresh = 0.558 |
| Limitations | 2 kg of blanched olive leaves per drying batch (30 Kg blanched olive leaves/shift and 10 Kg of dried olive leaves/shift) with one cabinet dryer. |

Milling

Milling of dried olive leaves have been done with 500, 300, 250 and 200 microns screens, provided a pre-grinding step is performed. No noticeable overheating was observed during milling. Reducing the particle size of the powders from 500 to 200 microns helped to increase solubility and homogeneity of tea solutions.

| Process | Dried Leaf Milling |
|---|---|
| Lead Time | 6 kg of dried leaves/h |
| Labor | One person to load and unload the mill |
| Machinery | SR 300 Retch mill with a GM 300 pre-mill (30 kg/h max capacity). |
| Conditions | Powder is obtained with particle size <200 microns without overheating |
| Limitations | 48 kg of dried milled powder can be obtained per daily labor shift |

Comparison of total soluble phenolics and antioxidant capacity of olive leaf powders with different blanching and drying processes against a commercial olive leaf powder. Infrared blanching and hot-air drying resulted in significantly higher total soluble phenolics and antioxidant capacity in final powders than any other processing method, including infrared blanching and freeze drying.

| Sample description | Total soluble phenolics (mg Gallic Acid/g d.w.) | Antioxidant capacity (μg Trolox/g d.w.) |
|---|---|---|
| Infrared blanching, 1.5 min; hot-air dried for 30 min | 28.653 ± 0.722$^f$ | 105,342 ± 2,804$^f$ |
| Steam blanching, 10 min; hot-air dried for 40 min | 23.307 ± 0.456$^c$ | 86,500 ± 1,054$^d$ |
| No blanching, hot-air dried for 50 min | 18.113 ± 0.501$^b$ | 57,946 ± 984$^b$ |
| Infrared blanching, 1.5 min; freeze-dried for 3 days | 26.103 ± 0.231$^e$ | 98,467 ± 3,122$^e$ |
| Steam blanching, 10 min; freeze-dried for 3 days | 21.263 ± 0.869$^d$ | 76,509 ± 383$^c$ |
| No blanching, freeze-dried for 3 days | 17.613 ± 0.155$^b$ | 54,610 ± 779$^b$ |
| Olive leaf tea from Olivus, Inc. | 12.240 ± 0.405$^a$ | 41,825 ± 1,554$^a$ |

What is claimed is:

1. A method of producing olive leaf powder, the method comprising:
    (a) blanching fresh olive leaves using infrared radiation;
    (b) drying the blanched olive leaves using hot air drying at a temperature between about 70° C. and about 95° C. for between about 15 and about 40 minutes; and (c) milling the dried olive leaves, thereby producing an olive leaf powder.

2. The method of claim 1, wherein the infrared radiation has a wavelength between 3 and 8 microns.

3. The method of claim 1, wherein the infrared radiation has a wavelength of about 4.5 microns.

4. The method of claim 1, wherein the step of blanching is carried out for about 30 seconds to about 5 minutes.

5. The method of claim 4, wherein the step of blanching is carried out for between about 1 minute and about 2 minutes.

6. The method of claim 1, wherein the step of blanching results in a surface temperature on the olive leaves of between about 200° F. and about 300° F.

7. The method of claim 6, wherein the temperature is about 260° F.

8. The method of claim 1, wherein the step of hot air drying is carried out at a temperature between about 70° C. and about 90° C.

9. The method of claim 8, wherein the temperature is about 80° C.

10. The method of claim 1, wherein the step of hot air drying is carried out for between about 25 and about 35 minutes.

11. The method of claim 10, wherein the step of hot air drying is carried out for about 35 minutes.

12. The method of claim 1, further comprising the step of separating the leaf blades from the leaf midrib and petioles, prior to the step of milling the dried olive leaves.

13. The method of claim 1, further comprising the step of grinding the olive leaves prior to the step of milling.

14. The method of claim 1, wherein the step of milling results in a powder with a particle size less than about 500 microns.

15. The method of claim 14, wherein the particle size is less than about 200 microns.

16. An olive leaf powder produced by a method comprising:
(a) blanching fresh olive leaves using infrared radiation;
(b) drying the blanched olive leaves using hot air drying at a temperature between about 70° C. and about 95° C. for between about 15 and about 40 minutes; and
(c) milling the dried olive leaves, thereby producing an olive leaf powder.

17. A food product comprising the olive leaf powder of claim 16.

18. A pharmaceutical composition comprising the olive leaf powder of claim 16.

19. A cosmetic composition comprising the olive leaf powder of claim 16.

20. An antimicrobial composition comprising the olive leaf powder of claim 16.

* * * * *